United States Patent [19]

Scovill et al.

[11] 4,440,771

[45] Apr. 3, 1984

[54] 2-ACETYL QUINOLINE THIOSEMICARBAZONES USEFUL IN TREATMENT OF GONORRHEA, MALARIA OR BACTERIAL INFECTIONS

[75] Inventors: John P. Scovill, Silver Spring; Daniel L. Klayman, Chevy Chase; Samuel P. Massie, Laurel, all of Md.; Steven D. Grant, Lander, Wyo.; Armando Gonzalez, Orlando, Fla.; Norman E. Morrison, Baltimore, Md.; Arthur S. Dobek, Silver Spring, Md.

[73] Assignee: The United States of America as represented by the Secretary of the Army, Washington, D.C.

[21] Appl. No.: 348,462

[22] Filed: Feb. 12, 1982

[51] Int. Cl.$^3$ .................. C07D 215/12; A61K 31/47
[52] U.S. Cl. .............................. 424/258; 424/248.51; 424/250; 424/257; 260/244.4; 544/128; 544/363; 546/15; 546/104; 546/168; 546/175
[58] Field of Search .................. 424/258, 250, 248.51, 424/257; 546/175, 168, 15, 104; 260/244.4; 544/128, 363

[56] References Cited

U.S. PATENT DOCUMENTS 4,317,776  3/1982  Klayman et al. ............... 260/244.4

FOREIGN PATENT DOCUMENTS 54-128583 10/1979  Japan ................................. 424/258
1100870  1/1968  United Kingdom ............... 546/175

OTHER PUBLICATIONS

French, et al., J. Med. Chem., vol. 17, No. 2, pp. 172-181, (1974).
Jorgenson, Organic Reactions, vol. 18, pp. 1-97, (1970).
Fujikawa, et al., Chemical Abstracts, vol. 68, 29557b, (1968).
Hogarth, et al., Chemical Abstracts, vol. 44, 4143a, (1950).
Knotz, Chemical Abstracts, vol. 67, 43724q, (1967).
Borsche, et al., Chemical Abstracts, vol. 31, 4069, (1937).

Primary Examiner—Donald G. Daus
Assistant Examiner—Diana G. Rivers
Attorney, Agent, or Firm—William G. Gapcynski; Arthur I. Spechler; Werten F. W. Bellamy

[57] ABSTRACT

This invention relates to the preparation and use of various 2-acetyl quinoline thiosemicarbazones which are substituted on the 4-nitrogen atom. These compounds are useful in the treatment of gonorrhea and, in addition, many are useful either in the treatment of malaria or bacterial infections, such as leprosy and meningitis.

54 Claims, No Drawings

2-ACETYL QUINOLINE THIOSEMICARBAZONES USEFUL IN TREATMENT OF GONORRHEA, MALARIA OR BACTERIAL INFECTIONS

The invention described herein may be manufactured and used by or for the Government for governmental purposes without the payment of any royalties thereon or therefor.

DETAILED DESCRIPTION OF THE INVENTION

This invention relates to the use of the following compounds and their pharmaceutically-acceptable acid addition salts in the treatment of gonorrhea, malaria, or bacterial infections such as leprosy and meningitis:

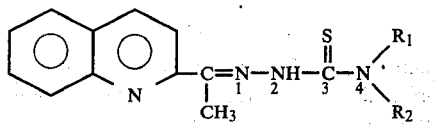

wherein $R_1$ is alkyl, preferably having one to 12 carbon atoms or, more preferably, one to six carbon atoms; cycloalkyl, preferably having three to ten carbon atoms; substituted alkyl wherein the alkyl group preferably has one to 12 carbon atoms and the substituent group is amino, alkylamino (preferably one to four carbon atoms), dialkylamino (preferably one to four carbon atoms in each alkyl group), cycloalkyl (preferably three to ten carbon atoms), hydroxy, COO alkyl (preferably one to four carbon atoms in the alkyl group), phenyl, or pyridyl; alkenyl, preferably having two to six carbon atoms; alkynyl, preferably having three to six carbon atoms; substituted benzyl wherein the substituent is methyl or phenyl on the alpha carbon atom, or the substituent is alkyl (preferably methyl), dialkyl (preferably dimethyl), halo, dihalo, or alkoxy (preferably ethoxy) on the phenyl ring; adamantyl; phenyl; naphthyl; substituted phenyl or substituted naphthyl wherein the ring is mono-, di-, or trisubstituted and the substituents are alkyl (preferably one to four carbon atoms), halo (preferably fluoro), alkoxy (preferably one to four carbon atoms), hydroxy, phenoxy, trifluoromethyl, dialkyl (preferably dimethyl) amino, dialkylaminoalkyl (preferably diethylaminomethyl), or pyridyl; thienyl; indolyl; furyl; acridyl; quinolyl; or pyridazinyl; and $R_2$ is hydrogen or is selected from the group of radicals listed above for $R_1$, in which case $R_1$ and $R_2$ may be the same or different; or $R_1$ and $R_2$ are taken together with the nitrogen atom to which they are attached to form a heterocyclic ring selected from the group consisting of:
(1) alkylenimino;
(2) alkylenimino which may contain one double bond and/or is mono- or disubstituted with alkyl (preferably one to four carbon atoms), hydroxy, phenyl, or benzyl;
(3) alkylenimino which is either bridged by an alkylene group (preferably two carbon atoms) or is fused to a phenyl ring; or is attached by a spiro linkage to an ethylene ketal group;
(4) homopiperazinyl; homopiperazinyl substituted with alkyl (preferably one to four carbon atoms); piperazinyl; or piperazinyl substituted with alkyl (preferably one to four carbon atoms), dialkyl (preferably one to four carbon atoms in each alkyl group), phenyl, COO alkyl (preferably one to four carbon atoms in the alkyl group), trifluoromethylphenyl, halophenyl, benzyl, or pyridyl; and
(5) morpholino, dialkyl (preferably one to four carbon atoms in each alkyl group) morpholino.

When $R_1$ and $R_2$ are taken together with the nitrogen atom to which they are attached, the resulting heterocyclic ring is preferably one of the following: azetidino; pyrrolidino; 2,5-dimethyl pyrrolidino; piperidino;

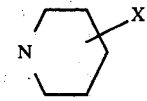

(wherein X is 2-methyl, 3-methyl, 4-methyl, 2-ethyl, 4-hydroxy, 4-phenyl, or 4-benzyl); hexamethylenimino; octamethylenimino; dodecamethylenimino; 2,6-dimethyl piperidino; 3,5-dimethyl piperidino; morpholino; 3,5-dimethylmorpholino;

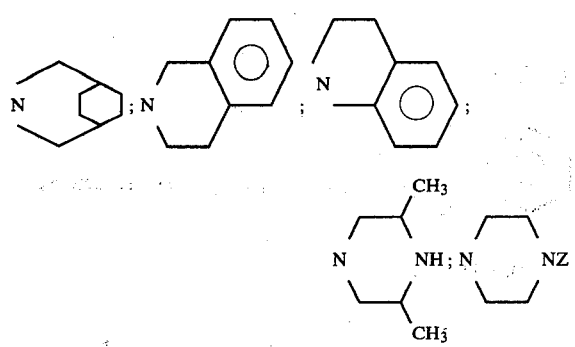

(wherein Z is methyl, phenyl, 3-trifluoromethyl phenyl, benzyl, COO Et, 3-pyridyl, 2-pyridyl, or 4-fluorophenyl);

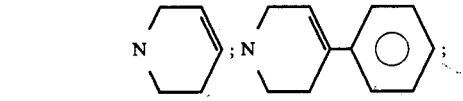

azacyclotridecyl;

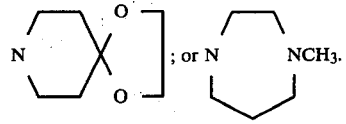

In this disclosure, it is understood that COO alkyl represents the alkyl carboxylic acid ester; for example, COO Et represents the ethyl carboxylic acid ester.

While evidence indicates that all of the above-described compounds and their pharmaceutically-acceptable acid addition salts are useful in the treatment of gonorrhea (gonorrhoeae), in addition many of the compounds and salts are useful either in the treatment of malaria or bacterial infections, such as leprosy and meningitis. Such use of the above-described compounds and salts is included in the present invention. Moreover, the above-described compounds per se, and their pharmaceutically-acceptable acid addition salts, are included in the invention provided that: when $R_2$ is hydrogen, then $R_1$ cannot be ethyl, isopropyl, or monochlorophenyl.

With respect to the pharmaceutically-acceptable acid addition salts of this invention, it will be apparent to those of ordinary skill in the art that such salts are contemplated only where the structural features of the compounds permit their preparation. As non-limiting examples of acids used to prepare such salts are mentioned hydrochloric and hydrobromic acids.

SYNTHETIC PROCEDURES

A key intermediate (2-acetylquinoline) was prepared by two routes, one of which was described by K. N. Campbell et al in the *Journal of American Chemical Society*, Vol. 68, page 1840 (1946). The second, involves the treatment of quinaldic acid (obtained by the method of Campbell et al) with methyllithium in anhydrous tetrahydrofuran according to the technique of M. Jorgenson disclosed in *Organic Reactions*, Vol. 18, (1970). The synthetic procedures may be illustrated as follows:

Step 1

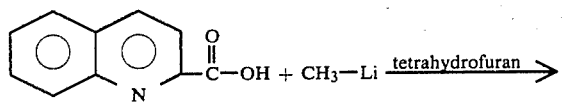

(Quinaldic Acid)

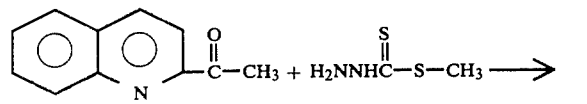

(2-Acetylquinoline)

Step 2

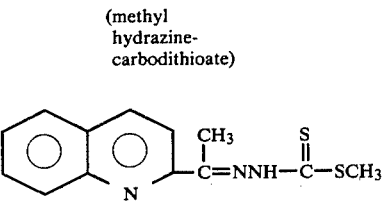

(methyl hydrazine-carbodithioate)

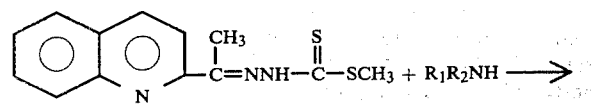

(methyl 3-[1-(2-quinolyl)-ethylidene]hydrazine carbodithioate)

Step 3

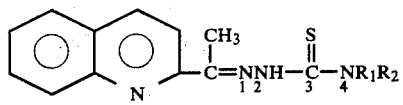

(2-acetylquinoline $N^4$—monosubstituted and $N^4,N^4$—disubstituted thiosemicarbazones)

WORKING EXAMPLES

The working examples set forth below illustrate the preparation of representative compounds and salts, but in no way limit the scope of the invention.

EXAMPLE 1

2-Acetylquinoline

Quinaldic acid (2.76 grams, 0.017 mole) was dissolved in 100 ml of dried tetrahydrofuran. Then 25 ml of 1.6 M (0.04 mole) of methyl lithium was added using a syringe. Reaction appeared immediate. The solution was stirred and heated under reflux for two hours and then poured into 600 ml of ice water. The ketone (2-acetylquinoline) was extracted with four 25 ml portions of ethyl ether which, after drying, was removed by rotary evaporation to yield ca. 1.0 g (ca. 40%) of 2-acetylquinoline.

EXAMPLE 2

Methyl 3-[1-(2-quinolyl)ethylidene]hydrazine carbodithioate

In 100 ml of 2-propanol was placed 18.9 grams (0.11 mole) of 2-acetylquinoline and 13.0 grams (0.107 mole) of methyl hydrazine-carbodithioate. The mixture was mechanically stirred for two hours. The resulting solid was filtered, washed with cold 2-propanol and dried to yield 2.5 grams (83%) of product, melting point 192°–194° C.

The thiosemicarbazones of this invention were prepared by reacting the intermediate prepared in Example 2 with various amines in the presence of methanol or ethanol. More specifically, methanol was used if the amine reactant was non-aromatic and ethanol was used when the amine reactant was aromatic.

EXAMPLE 3

1-Azacycloheptane-1-thiocarboxylic Acid 2-[1-(2-quinolyl)ethylidene]-hydrazide

To 50 ml of methanol, 1.10 grams (0.011 mole) hexamethyleneimine and a 3.00 grams (0.11 mole) of methyl 3-[1-(2-quinolyl)ethylidene hydrazine carbodithioate was added and heated under reflux overnight. The release of methyl mercaptan was tested for by placing a piece of filter paper moistened with a solution of lead acetate over the mouth of the condenser. A bright yellow color would appear in the presence of methyl mercaptan. The reaction was considered complete when only a slight color change was noticed. Water was added until the solution turned cloudy and the mixture was then cooled. The mixture was filtered after cooling overnight and the crude product (3.0 grams) was collected. Recrystallization was carried out from boiling methanol. The weight of the recrystallized product was 2.87 grams (80%), melting point 129°–131° C.

TABLE 1

| COMPOUND | Color | Molecular Weight | Melting Point, °C. | Element | Calculated | Found |
|---|---|---|---|---|---|---|
| Example 2 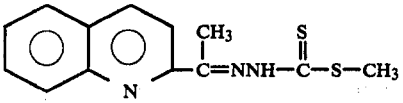 Methyl 3-[1-(2-quinolyl)ethylidene]hydrazine carbodithioate | Yellow | 275.40 | 192–194 | C<br>H<br>N<br>S | 56.70<br>4.76<br>15.26<br>23.29 | 57.20<br>4.78<br>15.01<br>23.02 |
| Example 3 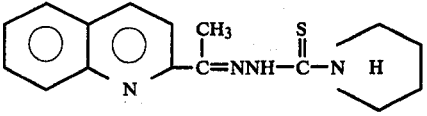 1-Azecycloheptane-1-thiocarboxylic acid 2-[1-(2-quinolyl)ethylidene]hydrazide | Orange | 326.47 | 129–131 | C<br>H<br>N<br>S | 66.22<br>6.79<br>17.16<br>9.82 | 66.40<br>6.86<br>16.97<br>9.80 |
| Example 4 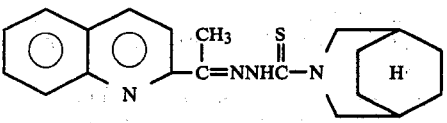 3-Azabicyclo[3.2.2]noname-3-thiocarboxylic acid 2-[1-(2-quinolyl)ethylidene]hydrazide | Yellow | 352.50 | 165–167 | C<br>H<br>N<br>S | 68.15<br>6.86<br>15.89<br>9.10 | 68.38<br>6.92<br>15.89<br>8.81 |
| Example 5 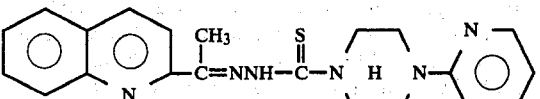 4-(2-Pyridyl)piperidinothiocarboxylic acid 2-(1-(2-quinolyl)ethylidene)hydrazide | Orange | 376.33 | 159–161 | C<br>H<br>N<br>S | 64.59<br>5.68<br>21.52<br>8.21 | 64.54<br>5.78<br>21.39<br>8.10 |

TABLE 2

| COMPOUND | Color | Molecular Weight | Melting Point, °C. | Element | Calculated | Found |
|---|---|---|---|---|---|---|
| Example 6 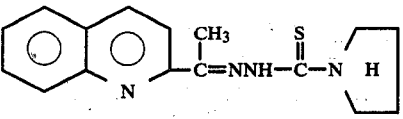 Pyrrolidine-1-thiocarboxylic acid 2-[1-(2-quinolyl)ethylidene]hydrazide | Yellow | 284.25 | 172–174 | C<br>H<br>N<br>S | 64.40<br>6.08<br>18.78<br>10.74 | 64.46<br>6.05<br>18.89<br>10.73 |
| Example 7 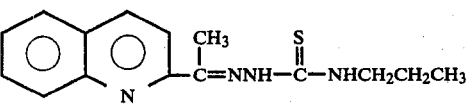 1-Propylaminothiocarboxylic acid 2-[1-(2-quinolyl)ethylidene]hydrazide | Yellow | 272.26 | 168–171 | C<br>H<br>N<br>S | 62.91<br>6.34<br>19.56<br>11.20 | 62.82<br>6.35<br>19.55<br>11.16 |
| Example 8 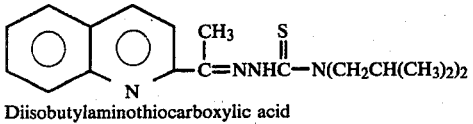 Diisobutylaminothiocarboxylic acid 2-[1-(2-quinolyl)ethylidene]hydrazide | Orange | 342.35 | 145–146 | C<br>H<br>N<br>S | 67.38<br>7.92<br>15.71<br>8.99 | 67.47<br>7.87<br>15.81<br>9.03 |

UTILITY

The compounds of this invention possess medicinal activity. More specifically, evidence indicates that the compounds demonstrate activity against *Neisseria gonorrhoeae*, including penicillin-resistant strains, and are therefore useful in the treatment of gonorrhea. In addition, many compounds and salts are useful either in the treatment of malaria (active against *Plasmodium begheri*) or bacterial infection (active against *Staphylococcus aureus; Neisseria meningitidis;* or *Mycobacterium smegmatis.*

Several tests have been made to determine the activity of the compounds of this invention. In order to guide one of ordinary skill in the practice of the invention, these tests are described below, as well as results obtained in each test with a representative sampling of compounds:

Compounds are coded as follows, 3F 1-Azacycloheptane-1-thiocarboxylic acid 2-1[1-(2-quinolyl)ethylidene]hydrazide 3G 3-Azabicyclo[3.2.2]none-3-thiocarboxylic acid 2-[1-(2-quinolyl)ethylidene]hydrazide 3H 4-(2-Pyridyl)piperidinothiocarboxylic acid 2-(1-(2-quinolyl)ethylidene)hydrazide 3I Pyrrolidine-1-thiocarboxylic acid 2-[1-(2-quinolyl)ethylidene]hydrazide 3J I-Propylaminothiocarboxylic acid 2-[1-(2-quinolyl)ethylidene]hydrazide 3K Diisobutylaminothiocarboxylic acid 2-[1-(2-quinolyl)ethylidene]hydrazide

TEST 1

Compounds were tested against five isolates of *Staphylococcus aureus*. The bacteria used were isolated from patients at the Walter Reed Army Medical Center, Washington, D.C. The test procedure used was the macro broth dilution method in duplicate as outlined by J. C. Sherris on pages 414–415 in "Manual of Clinical Microbiology," 2nd Ed., E. Lennette, E. H. Spaulding, and J. P. Truant, Ed. (American Society for Microbiology, Washington, D.C., 1974). Each compound was dissolved in Dimethyl Sulfoxide (DMSO) (12.8 mg/ml) and then diluted with Mueller-Hinton broth to obtain the desired dilutions. Tubes containing the hightest quantities of DMSO with no compound present were run as controls. The results were read after 24 hours and are summarized in Tables 3 and 4 below. DMSO controls showed no inhibition of bacterial growth.

TABLE 3

| | Minimum Inhibitory Concentration (µg/ml) | | | | |
|---|---|---|---|---|---|
| | *Staphylococcus aureus* isolates | | | | |
| Compound | I | II | III | IV | V |
| 3F | 16 | 16 | 16 | 16 | 16 |
| 3G | 16 | 16 | 16 | 16 | 16 |
| 3H | 16 | 16 | 16 | 16 | 16 |
| 3I | ≦.25 | 0.5 | 0.5 | ≦.25 | ≦.25 |
| 3K | 16 | 16 | 16 | 16 | 16 |

TEST 2

Compounds were tested against five isolates of *Neisseria meningitidis*. The bacterial isolates were provided by the Department of Bacterial Diseases of the Walter Reed Army Institute of Research. The test procedure used was the macro broth dilutuon method in duplicate outlined by J. C. Sherris on pages 414–415. The test compounds and controls were prepared as in Test 1. Ampicillin and penicillin standards were initially diluted as described by J. C. Sherris on pages 411–412 followed by dilution with Mueller-Hinton broth. The tubes were incubated at 37° C. under 5–10% carbon dioxide. The test results were read after 24 hours and are summarized in Table 4. DMSO controls showed no inhibition of bacterial growth.

TABLE 4

| | Minimum Inhibitory Concentration (µg/ml) | | | | |
|---|---|---|---|---|---|
| | *Neisseria meningitidis* isolates | | | | |
| Compound | 7957 | 7990 | 8005 | 8006 | 8011 |
| 3F | <0.062 | 0.125 | 0.25 | 0.25 | 0.25 |

TABLE 4-continued

| | Minimum Inhibitory Concentration (µg/ml) | | | | |
|---|---|---|---|---|---|
| | *Neisseria meningitidis* isolates | | | | |
| Compound | 7957 | 7990 | 8005 | 8006 | 8011 |
| 3G | 0.125 | 1 | 1 | 0.5 | 0.5 |
| 3H | >1 | >1 | >1 | >1 | >1 |
| 3I | 0.062 | 0.125 | 0.125 | 0.125 | 0.125 |
| 3K | 0.125 | 0.5 | 0.5 | 1 | 0.5 |
| Penicillin | 0.031 | 0.031 | — | 0.031 | 0.031 |
| Ampicillin | 0.008 | 0.008 | 0.008 | 0.016 | 0.016 |

TEST 3

Compounds were tested against 35 *Neisseria gonorrhoeae* isolates. The bacteria used were provided by the Department of Bacterial Diseases of the Walter Reed Amry Institute of Research. The test procedure used was the agar dilution method in duplicate as outlined by J. S. Sherris on pages 411–412. GC Medium (Difco) with a 2% defined supplement added as described by D. S. Kellogg et al [*J. Bact.* 85:1274–1279 (1963)] was used as the media. The compounds were dissolved in DMSO (1.0 mg/ml), diluted with GC broth (GC Medium without agar) to the appropriate concentration, and added to the GC Medium at 55°–56° C. The latter was then poured and allowed to solidify. A penicillin standard was also prepared with initial dilutions as described by J. C. Sherris followed by dilutions with GC broth and addition to the GC Medium at 55°–56° C. The inoculum was 1:200 CG broth dilution of a suspension of colony isolates after the suspension was adjusted visually to the turbidity standard described by J. M. Matsen and A. L. Barr on page 422 in "Manual of Clinical Microbiology," 2nd Ed., E. Lennette, E. H. Spaulding, and J. P. Truant, Ed. (American Society for Microbiology, Washington, D.C., 1974). The plates were inoculated with a replicator and incubated at 37° C. under 5–10% carbon dioxide. The results were read 24 hours and are summarized in Table 5. DMSO controls showed no inhibition.

TABLE 5

| Minimum Inhibitory Concentration (µg/ml) | |
|---|---|
| Compound | *Neisseria gonorrhoeae* isolates |
| 3F | 0.25–0.5 |
| 3G | 0.5–1 |
| 3H | 0.125–0.5 |
| 3I | 0.125–0.25 |
| 3K | >1 |
| Penicillin | 0.062–16 |

TEST 4

Compounds were tested against three strains of *Mycobacterium smegmatis*. The test procedure used was as mentioned by N. E. Morrison [*Int. J. of Leprosy* 39:34–43 (1971)]. The results are summarized in Table 6. The strain numbers refer to *Mycobacterium smegmatis* ATCC 607 (I), a DDS-resistant daughter strain (II), and a Rifampin-resistant daughter strain (III), respectively.

TABLE 6

| | Minimum Inhibitory Concentration (µg/ml) | | |
|---|---|---|---|
| | *Mycobacterium smegmatis* strains | | |
| Compound | I | II | III |
| 3F | 2.5 | 15 | 10 |
| 3G | 4 | 15 | 10 |
| 3H | 2.5 | 10 | 5 |
| 3I | 0.6 | 3 | 1.5 |
| 3J | 1 | 4 | 2 |

TABLE 6-continued

| | Minimum Inhibitory Concentration (μg/ml) | | |
| --- | --- | --- | --- |
| | *Mycobacterium smegmatis* strains | | |
| Compound | I | II | III |
| 3K | 10 | >50 | >50 |
| DDS | 2 | 400 | — |
| Rifampin | 1 | — | 250 |

TEST 5

Compounds were tested against *Plasmodium berghei* KBG 173 malaria in mice following the procedure described by T. S. Osdene, P. B. Russell, and L. Rane [*J. Med. Chem.* 10:431–434 (1967)]. Five mice were tested at each dosage level. Mice surviving 60 days are considered cured. Toxicity is defined as a decrease in the mean survival time of the treated mice as compared to the control group. Activity is defined as a 100% increase in the mean survival time of the treated mice compared to the control group. The $ED_{50}$ is a computed estimate of the dose required to cure 50% of the mice. The results are summarized in Table 7.

TABLE 7

In vivo Antimalarial Activity of 2-Acetylquinoline Thiosemicarbazones against *Plasmodium berghei* in Mice

| | Dosage Level (mg/kg) | | | | |
| --- | --- | --- | --- | --- | --- |
| Compound | 40 | 80 | 160 | 320 | 640 |
| 3F | — | — | — | C(2/5) | C(4/5) |
| 3G | — | — | active | C(3/5) | C(3/5) |
| 3H | — | — | — | — | — |
| 3I | — | — | C(1/5) | C(5/5) | C(5/5) |
| 3K | — | — | — | active | active |

C = Cure

We claim:

1. A quinoline thiosemicarbazones compound of the formula

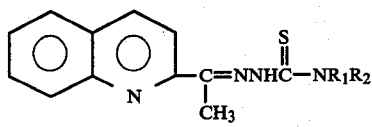

or a pharmaceutically-acceptable acid addition salt thereof wherein $R_1$ is alkyl of 1 to 12 carbon atoms; cycloalkyl of 3 to 10 carbon atoms; substituted alkyl of 1 to 12 carbon atoms (wherein the substituent is amino, alkylamino of 1 to 4 carbon atoms, dialkylamino of 1 to 4 carbon atoms in each alkyl group, cycloalkyl of 3 to 10 carbon atoms, hydroxy, COO alkyl of 1 to 4 carbon atoms, phenyl, or pyridyl); alkenyl of 2 to 6 carbon atoms; alkynyl of 3 to 6 carbon atoms; substituted benzyl (wherein the substituent is methyl or phenyl on the alpha carbon atom, or the substituent is methyl, dimethyl, halo, dihalo, or ethoxy on the phenyl ring); adamantyl; phenyl; naphthyl; substituted phenyl or substituted naphthyl (wherein the ring is mono-, di-, or trisubstituted and the substituents are alkyl of 1 to 4 carbon atoms, halo, alkoxy of 1 to 4 carbon atoms, hydroxy, phenoxy, trifluoromethyl, dimethylamino, diethylamino, or pyridyl; thienyl; indolyl; furyl; acridyl; quinolyl; or pyridazinyl; and $R_2$ is hydrogen or is selected from the group of radicals listed above for $R_1$, in which case $R_1$ and $R_2$ may be the same or different; or $R_1$ and $R_2$ are taken together with the nitrogen atom to which they are attached to form a heterocyclic ring selected from the group consisting of:
(1) alkylenimino having 3 to 13 carbon atoms;
(2) alkylenimino having 3 to 13 carbon atoms which may contain one double bond and/or is mono- or disubstituted with alkyl having 1 to 4 carbon atoms, hydroxy, phenyl, or benzyl;
(3) alkylenimino having 3 to 13 carbon atoms which is either bridged by an alkylene group having 1 to 3 carbon atoms, or is fused to a phenyl ring, or is attached by a spiro linkage to an ethylene ketal group;
(4) homopiperazinyl; homopiperazinyl substituted with alkyl having 1 to 4 carbon atoms; piperazinyl; or piperazinyl substituted with alkyl having 1 to 4 carbon atoms, dialkyl having 1 to 4 carbon atoms in each alkyl group, phenyl, COO alkyl having 1 to 4 carbon atoms in the alkyl group, trifluoromethylphenyl, halophenyl, benzyl, or pyridyl; and
(5) morpholino; dialkylmorpholino having 1 to 4 carbon atoms in each alkyl group;

provided that:
when $R_2$ is hydrogen, then $R_1$ cannot be ethyl, isopropyl, or monochlorophenyl.

2. A quinoline thiosemicarbazone compound of the formula

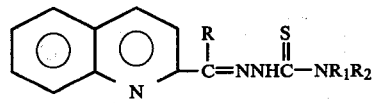

or a pharmaceutically-acceptable acid addition salt thereof wherein

R is methyl or ethyl; and $R_1$ is alkyl of one to 12 carbon atoms; cycloalkyl of three to ten carbon atoms; substituted alkyl of one to 12 carbon atoms (wherein the substituent is amino, alkylamino of one to four carbon atoms, dialkylamino wherein the alkyl groups each contain one to four carbon atoms, cycloalkyl of three to ten carbon atoms, hydroxy, COO alkyl wherein the alkyl group contains one to four atoms, phenyl, or pyridyl); alkenyl of two to six carbon atoms; alkynyl of three to six carbon atoms; substituted benzyl (wherein the substituent is methyl or phenyl on the alpha carbon atom, or the substituent is methyl, dimethyl, halo, dihalo, or ethoxy on the phenyl ring); adamantyl; phenyl; naphthyl; substituted phenyl or substituted naphthyl (wherein the ring is mono-, di-, or trisubstituted and the substituents are alkyl of one to four carbon atoms, halo, alkoxy of one to four carbon atoms, hydroxy, phenoxy, trifluoromethyl, dimethylamino, diethylaminomethyl, or pyridyl; thienyl; indolyl; furyl; acridyl; quinolyl; or pyridazinyl; and $R_2$ is hydrogen or is selected from the group of radicals listed above for $R_1$, in which case $R_1$ and $R_2$ may be the same or different; or $R_1$ and $R_2$ are taken together with the nitrogen atom to which they are attached to form a heterocyclic ring selected from the group consisting of:

azetidino; pyrrolidino; 2,5-dimethylpyrrolidino; piperidino;

(wherein X is 2-methyl, 3-methyl, 4-methyl, 2-ethyl, 4-hydroxy, 4-phenyl, or 4benzyl); hexamethylenimino; octamethylenimino; dodecamethylenimino; 2,6-dimethyl piperidino; 3,5-dimethyl piperidino; morpholino; 3,5-dimethylmorpholino;

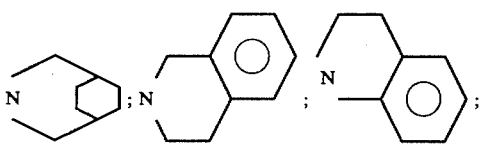

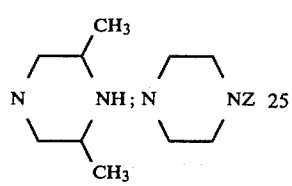

(wherein Z is methyl, phenyl, 3-trifluoromethylphenyl, benzyl, COOEt, 3-pyridyl, 2-pyridyl, or 4-fluorophenyl); azacyclotridecyl;

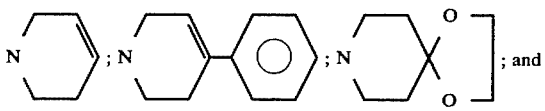

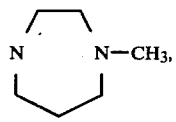

provided that:
when $R_2$ is hydrogen, then $R_1$ cannot be ethyl, isopropyl, or monochlorophenyl.

3. A compound or salt of claim 1 wherein $NR_1R_2$ is

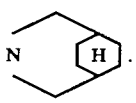

4. A compound or salt of claim 1 wherein $NR_2R_2$ is

5. A compound or salt of claim 1 wherein $NR_1R_2$ is $NHCH_2CH_2CH_3$.

6. A compound or salt of claim 1 wherein $NR_1R_2$ is $N(CH_2CH(CH_3)_2)_2$.

7. A compound or salt of claim 1 wherein $NR_1R_2$ is azetidino.

8. A compound or salt of claim 1 wherein $NR_1R_2$ is piperidino.

9. A compound or salt of claim 1 wherein $NR_1R_2$ is 2-methylpiperidino.

10. A compound or salt of claim 1 wherein $NR_1R_2$ is ethylpiperidino.

11. A compound or salt of claim 1 wherein $NR_1R_2$ is hexamethylenimino.

12. A compound or salt of claim 1 wherein $NR_1R_2$ is azacyclotridecyl.

13. A compound or salt of claim 1 wherein $NR_1R_2$ is

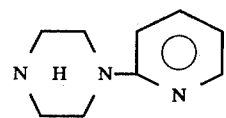

14. A compound or salt of claim 1 wherein $NR_1R_2$ is

15. A compound or salt of claim 1 wherein $NR_1R_2$ is

16. A compound or salt of claim 1 wherein $R_1$ and $R_2$ are each methyl.

17. A compound or salt of claim 1 wherein $R_1$ is 1-adamantyl and $R_2$ is hydrogen.

18. A compound or salt of claim 1 wherein $R_1$ is allyl and $R_2$ is hydrogen.

19. A compound or salt of claim 1 wherein $R_1$ is cyclohexyl and $R_2$ is hydrogen.

20. A compound or salt of claim 1 wherein $R_1$ is diethylaminoethyl and $R_2$ is hydrogen.

21. A compound or salt of claim 1 wherein $R_1$ is 3-fluorophenyl and $R_2$ is hydrogen.

22. A compound or salt of claim 1 wherein $R_1$ and $R_2$ are each isobutyl.

23. A compound or salt of claim 1 wherein $R_1$ is methyl and $R_2$ is cyclohexyl.

24. A compound or salt of claim 1 wherein $R_1$ is 2-methylbenzyl and $R_2$ is hydrogen.

25. A compound or salt of claim 1 wherein $R_1$ is 2-pyridyl and $R_2$ is hydrogen.

26. A compound or salt of claim 1 wherein $R_1$ is 1,1,3,3-tetramethylbutyl and $R_2$ is hydrogen.

27. A compound or salt of claim 1 wherein $R_1$ is 2-picolyl and $R_2$ is hydrogen.

28. A method for treating an animal infected with leprosy by administering to said animal a therapeutically effective amount of a quinoline thiosemicarbazone compound of the formula

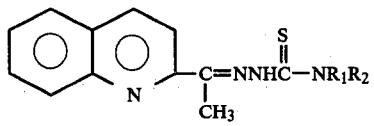

or a pharmaceutically-acceptable acid addition salt thereof wherein $R_1$ is alkyl of 1 to 12 carbon atoms; cycloalkyl of 3 to 10 carbon atoms; substituted alkyl of 1 to 12 carbon atoms (wherein the substituent is amino, alkylamino of 1 to 4 carbon atoms, dialkylamino of 1 to 4 atoms in each alkyl group, cycloalkyl of 3 to 10 carbon atoms, hydroxy, COO alkyl of 1 to 4 carbon atoms, phenyl, or pyridyl); alkenyl of 2 to 6 carbon atoms; alkynyl of 3 to 6 carbon atoms; substituted benzyl (wherein the substituent is methyl or phenyl on the alpha carbon atom, or the substituent is methyl, dimethyl, halo, dihalo, or ethoxy on the phenyl ring); adamantyl; phenyl; naphthyl; substituted phenyl or substituted naphthyl (wherein the ring is mono-, di-, or trisubstituted and the substituents are alkyl of 1 to 4 carbon atoms, halo, alkoxy of 1 to 4 carbon atoms, hydroxy, phenoxy, trifluoromethyl, dimethylamino, diethylamino, or pyridyl; thienyl; indolyl; furyl; acridyl; quinolyl; or pyridazinyl; and $R_2$ is hydrogen or is selected from the group of radicals listed above for $R_1$, in which case $R_1$ and $R_2$ may be the same or different; or $R_1$ and $R_2$ are taken together with the nitrogen atom to which they are attached to form a heterocyclic ring selected from the group consisting of:
(1) alkylenimino having 3 to 13 carbon atoms;
(2) alkylenimino having 3 to 13 carbon atoms which may contain one double bond and/or is mono- or disubstituted with alkyl, hydroxy, phenyl, or benzyl;
(3) alkylenimino having 3 to 13 carbon atoms which is either bridged by an alkylene group having 1 to 3 carbon atoms, or is fused to a phenyl ring, or is attached by a spiro linkage to an ethylene ketal group;
(4) homopiperazinyl; homopiperazinyl substituted with alkyl having 1 to 4 carbon atoms; piperazinyl; or piperazinyl substituted with alkyl having 1 to 4 carbon atoms, dialkyl having 1 to 4 carbon atoms in each alkyl group, phenyl, COO alkyl having 1 to 4 carbon atoms in the alkyl group, trifluoromethylphenyl, halophenyl, benzyl, or pyridyl; and
(5) morpholino; dialkylmorpholino having 1 to 4 carbon atoms in each alkyl group;
provided that:
when $R_2$ is hydrogen, then $R_1$ cannot be ethyl, isopropyl, or monochlorophenyl.

29. The method of claim 28 wherein the quinoline thiosemicarbazone compound is 1-azacycloheptane-1-thiocarboxylic acid 2-[1-(2-quinolyl)ethylidene]hydrazide.

30. The method of claim 28 wherein the quinoline thiosemicarbazone compound is 3-azabicyclo[3.2.2]nonane-3-thiocarboxylic acid 2-[1-(2-quinolyl)ethylidene]hydrazide.

31. The method of claim 28 wherein the quinoline thiosemicarbazone compound is 4-(2-Pyridyl)piperidinothiocarboxylic acid 2-[1-(2-quinolyl)ethylidene]hydrazide.

32. The method of claim 28 wherein the quinoline thiosemicarbazone compound is Pyrrolidine-1-thiocarboxylic acid 2-[1-(2-quinolyl)ethylidene]hydrazide.

33. The method of claim 28 wherein the quinoline thiosemicarbazone compound is 1-Propyl aminothiocarboxylic acid 2-[1-(2-quinolyl)ethylidene]hydrazide.

34. The method of claim 28 wherein the quinoline thiosemicarbazone compound is Diisobutylaminothiocarboxylic acid 2-[1-(2-quinolyl)ethylidene]hydrazide.

35. A method for treating an animal having a malarial infection by administering to said animal a therapeutically effective amount of a quinoline thiosemicarbazone compound of the formula

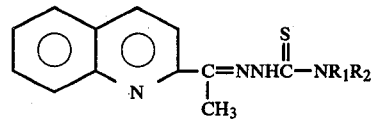

or a pharmaceutically-acceptable acid addition salt thereof wherein $R_1$ is alkyl of 1 to 12 carbon atoms; cycloalkyl of 3 to 10 carbon atoms; substituted alkyl of 1 to 12 carbon atoms (wherein the substituent is amino, alkylamino of 1 to 4 carbon atoms, dialkylamino of 1 to 4 carbon atoms in each alkyl group, cycloalkyl of 3 to 10 carbon atoms, hydroxy, COO alkyl of 1 to 4 carbon atoms, phenyl, or pyridyl); alkenyl of 2 to 6 carbon atoms; alkynyl of 3 to 6 carbon atoms; substituted benzyl (wherein the substituent is methyl or phenyl on the alpha carbon atom, or the substituent is methyl, dimethyl, halo, dihalo, or ethoxy on the phenyl ring); adamantyl; phenyl; naphthyl; substituted phenyl or substituted naphthyl (wherein the ring is mono-, di-, or trisubstituted and the substituents are alkyl of 1 to 4 carbon atoms, halo, alkoxy of 1 to 4 carbon atoms, hydroxy, phenoxy, trifluoromethyl, dimethylamino, diethylamino, or pyridyl; thienyl; indolyl; furyl; acridyl; quinolyl; or pyridazinyl; and $R_2$ is hydrogen or is selected from the group of radicals listed above for $R_1$, in which case $R_1$ and $R_2$ may be the same or different; or $R_1$ and $R_2$ are taken together with the nitrogen atom to which they are attached to form a heterocyclic ring selected from the group consisting of:
(1) alkylenimino having 3 to 13 carbon atoms;
(2) alkylenimino having 3 to 13 carbon atoms which may contain one double bond and/or is mono- or disubstituted with alkyl having 1 to 4 carbon atoms, hydroxy, phenyl, or benzyl;
(3) alkylenimino having 3 to 13 carbon atoms which is either bridged by an alkylene group having 1 to 3 carbon atoms, or is fused to a phenyl ring, or is attached by a spiro linkage to an ethylene ketal group;
(4) homopiperazinyl; homopiperazinyl substituted with alkyl having 1 to 4 carbon atoms; piperazinyl; or piperazinyl substituted with alkyl having 1 to 4 carbon atoms, dialkyl having 1 to 4 carbon atoms in each alkyl group, phenyl, COO alkyl having 1 to 4 carbon atoms in the alkyl group, trifluoromethylphenyl, halophenyl, benzyl, or pyridyl; and (5) morpholino; dialkylmorpholino having 1 to 4 carbon atoms in each alkyl group;
provided that:
when $R_2$ is hydrogen, then $R_1$ cannot be ethyl, isopropyl, or monochlorophenyl.

36. The method of claim 35 wherein the quinoline thiosemicarbazone compound is 1-Azacycloheptane-1-thiocarboxylic acid 2-[1-(2-quinolyl)ethlidene]hydrazide.

37. The method of claim 35 wherein the quinoline thiosemicarbazone compound is 3-Azabicyclo[3.2.2]nonane-3-thiocarboxylic acid 2-[1-(2-quinolyl)ethylidene]hydrazine.

38. The method of claim 35 wherein the quinoline thiosemicarbazone compound is Pyrrolidine-1-thiocarboxylic acid 2-[1-(2-quinolyl)ethylidene]hydrazide.

39. The method of claim 35 wherein the quinoline thiosemicarbazone compound is 1-Propylaminothiocarboxylic acid 2-[1-(2-quinolyl)ethylidene]hydrazide.

40. The method of claim 35 wherein the quinoline thiosemicarbazone compound is Diisobutylamino thiocarboxylic acid 2-[1-(2-quinolyl)ethylidene]hydrazide.

41. A method for treating an animal infected with gonorrhoeae by administering to said animal a therapeutically effective amount of a quinoline thiosemicarbazone compound of the formula

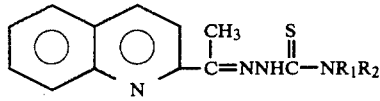

or a pharmaceutically-acceptable acid addition salt thereof wherein $R_1$ is alkyl of 1 to 12 carbon atoms; cycloalkyl of 3 to 10 carbon atoms; substituted alkyl of 1 to 12 carbon atoms (wherein the substituent is amino, alkylamino, dialkylamino of 1 to 4 carbon atoms, cycloalkyl of 3 to 10 carbon atoms, hydroxy, COO alkyl of 1 to 4 carbon atoms, phenyl, or pyridyl); alkenyl of 2 to 6 carbon atoms; alkynyl of 3 to 6 carbon atoms; substituted benzyl (wherein the substituent is methyl or phenyl on the alpha carbon atom, or the substituent is methyl, dimethyl, halo, dihalo, or ethoxy on the phenyl ring); adamantyl; phenyl; naphthyl; substituted phenyl or substituted naphthyl (wherein the ring is mono-, di-, or trisubstituted and the substituents are alkyl of 1 to 4 carbon atoms, halo, alkoxy of 1 to 4 carbon atoms, hydroxy, phenoxy, trifluoromethyl, dimethylamino, diethylamino, or pyridyl; thienyl; indolyl; furyl; acridyl; quinolyl; or pyridazinyl; and $R_2$ is hydrogen or is selected from the group of radicals listed above for $R_1$, in which case $R_1$ and $R_2$ may be the same or different; or $R_1$ and $R_2$ are taken together with the nitrogen atom to which they are attached to form a heterocyclic ring selected from the group consisting of:
(1) alkylenimino having 3 to 13 carbon atoms;
(2) alkylenimino having 3 to 13 carbon atoms which may contain one double bond and/or is mono- or disubstituted with alkyl having 1 to 4 carbon atoms, hydroxy, phenyl, or benzyl;
(3) alkylenimino having 3 to 13 carbon atoms which is either bridged by an alkylene group having 1 to 3 carbon atoms, or is fused to a phenyl ring, or is attached by a spiro linkage to an ethylene ketal group;
(4) homopiperazinyl; homopiperazinyl substituted with alkyl having 1 to 4 carbon atoms; piperazinyl; or piperazinyl substituted with alkyl having 1 to 4 carbon atoms, dialkyl having 1 to 4 carbon atoms in each alkyl group, phenyl, COO alkyl having 1 to 4 carbon atoms in the alkyl group, trifluoromethylphenyl, halophenyl, benzyl, or pyridyl; and
(5) morpholino; dialkylmorpholino having 1 to 4 carbon atoms in each alkyl group;
provided that:
when $R_2$ is hydrogen, then $R_1$ cannot be ethyl, isopropyl, or monochlorophenyl.

42. The method of claim 41 wherein the quinoline thiosemicarbazone compound is 1-Azacycloheptane-1-thiocarboxylic acid 2-[1-(2-quinolyl)ethylidene]hydrazide.

43. The method of claim 41 wherein the quinoline thiosemicarbazone compound is 3-Azabicyclo[3.2.2]noname-3-thiocarboxylic acid 2-[1-(2-quinolyl)ethylidene]hydrazide.

44. The method of claim 41 wherein the quinoline thiosemicarbazone compound is Diisobutylamino thiocarboxylic acid 2-[1-(2-quinolyl)ethylidene]hydrazide.

45. The method of claim 41 wherein the quinoline thiosemicarbazone compound is Pyrrolidine-1-thiocarboxylic acid 2-[1-(2-quinolyl)ethylidene]hydrazide.

46. The method of claim 41 wherein the quinoline thiosemicarbazone compound is 1-Propylaminothiocarboxylic acid 2-[1-(2-quinolyl)ethylidene]hydrazide.

47. A method for treating an animal infected with meningitis by administering to said animal a therapeutically effective amount of a quinoline thiosemicarbazone compound of the formula

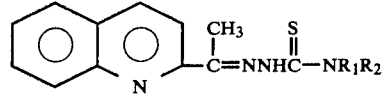

or a pharmaceutically-acceptable acid addition salt thereof wherein

Ris alkyl of 1 to 12 carbon atoms; cycloalkyl of 3 to 10 carbon atoms; substituted alkyl of 1 to 12 carbon atoms (wherein the substituent is amino, alkylamino of 1 to 4 carbon atoms, dialkylamino of 1 to 4 carbon atoms in each alkyl group, cycloalkyl of 3 to 10 carbon atoms, hydroxy, COO alkyl of 1 to 4 carbon atoms, phenyl, or pyridyl); alkenyl of 2 to 6 carbon atoms; alkynyl of 3 to 6 carbon atoms; substituted benzyl (wherein the substituent is methyl or phenyl on the alpha carbon atom, or the substituent is methyl, dimethyl, halo, dihalo, or ethoxy on the phenyl ring); adamantyl; phenyl; naphthyl; substituted phenyl or substituted naphthyl (wherein the ring is mono-, di-, or trisubstituted and the substituents are alkyl of 1 to 4 carbon atoms, halo, alkoxy of 1 to 4 carbon atoms, hydroxy, phenoxy, trifluoromethyl, dimethylamino, diethylamino, or pyridyl; thienyl; indolyl; furyl; acridyl; quinolyl; or pyridazinyl; and $R_2$ is hydrogen or is selected from the group of radicals listed above for $R_1$, in which case $R_1$ and $R_2$ may be the same or different; or $R_1$ and $R_2$ are taken together with the nitrogen atom to which they are attached to form a heterocyclic ring selected from the group consisting of:
(1) alkylenimino having 3 to 13 carbon atoms;
(2) alkylenimino having 3 to 13 carbon atoms which may contain one double bond and/or is mono- or disubstituted with alkyl having 1 to 4 carbon atoms, hydroxy, phenyl, or benzyl;
(3) alkylenimino having 3 to 13 carbon atoms which is either bridged by an alkylene group having 1 to 3 carbon atoms, or is fused to a phenyl ring, or is attached by a spiro linkage to an ethylene ketal group;
(4) homopiperazinyl; homopiperazinyl substituted with alkyl having 1 to 4 carbon atoms; piperazinyl; or piperazinyl substituted with alkyl having 1 to 4 carbon atoms, dialkyl having 1 to 4 carbon atoms in each alkyl group, phenyl, COO alkyl having 1 to 4 carbon atoms in the alkyl group, trifluoromethylphenyl, halophenyl, benzyl, or pyridyl; and
(5) morpholino; dialkylmorpholino having 1 to 4 carbon atoms in each alkyl group;
provided that:
when $R_2$ is hydrogen, then $R_1$ cannot be ethyl, isopropyl, or monochlorophenyl.

48. The method of claim 47 wherein the quinoline thiosemicarbazone compound is 1-Azacycloheptane-1-thiocarboxylic acid 2-[1-(2-quinolyl)-ethylidene]hydrazide.

49. The method of claim 47 wherein the quinoline thiosemicarbazone compound is 3-Azabicyclo[3.2.2-]noname-3-thiocarboxylic acid 2-[1-(2-quinolyl)ethylidene]hydrazide.

50. The method of claim 47 wherein the quinoline thiosemicarbazone compound is 4-(2-Pyridyl)-piperadino thiocarboxzylic acid 2-[1-(2-quinolyl)ethylidene]hydrazide.

51. The method of claim 47 wherein the quinoline thiosemicarbazone compound is Pyrrolidine-1-thiocarboxylic acid 2-[1-(2-quinolyl)ethylidene]hydrazide.

52. The method of claim 47 wherein the quinoline thiosemicarbazone compound is 1-Propyl-aminothiocarboxylic acid 2-[1-(2-quinolyl)ethylidene]hydrazide.

53. The method of claim 47 wherein the quinoline thiosemicarbazone compound is Dissobutylaminothiocarboxylic acid 2-[1-(2-quinolyl)ethylidene]hydrazide.

54. A method for treating an animal which has a bacterial infection by administering to said animal a therapeutically effective amount of a quinoline thiosemicarbazone compound of claim 1.

* * * * *